US008852275B2

(12) United States Patent
Park

(10) Patent No.: US 8,852,275 B2
(45) Date of Patent: *Oct. 7, 2014

(54) INTRAOCULAR LENS SUPPORTER

(76) Inventor: Kyong Jin Park, Seoul (KR)

( * ) Notice: Subject to any disclaimer, the term of this patent is extended or adjusted under 35 U.S.C. 154(b) by 310 days.

This patent is subject to a terminal disclaimer.

(21) Appl. No.: 12/293,967

(22) PCT Filed: Sep. 21, 2007

(86) PCT No.: PCT/KR2007/004631
§ 371 (c)(1),
(2), (4) Date: Aug. 14, 2009

(87) PCT Pub. No.: WO2008/108523
PCT Pub. Date: Sep. 12, 2008

(65) Prior Publication Data
US 2009/0306774 A1 Dec. 10, 2009

(30) Foreign Application Priority Data
Mar. 8, 2007 (KR) .................. 10-2007-0022870

(51) Int. Cl.
*A61F 2/16* (2006.01)
(52) U.S. Cl.
CPC .............. *A61F 2/1613* (2013.01); *A61F 2/1694* (2013.01)
USPC .......... 623/6.38; 623/6.39; 623/6.4; 623/6.41
(58) Field of Classification Search
USPC ............................................. 623/6.38–6.41
See application file for complete search history.

(56) References Cited

U.S. PATENT DOCUMENTS

| 5,152,789 | A | 10/1992 | Willis |
| 6,972,033 | B2 | 12/2005 | McNicholas |
| 7,097,660 | B2 | 8/2006 | Portney |
| 2003/0135272 | A1 | 7/2003 | Brady et al. |
| 2004/0082994 | A1 | 4/2004 | Woods et al. |
| 2004/0082995 | A1* | 4/2004 | Woods .......... 623/6.34 |
| 2005/0107873 | A1* | 5/2005 | Zhou ............ 623/6.13 |

FOREIGN PATENT DOCUMENTS

| JP | 2006-503661 T | 2/2006 |
| WO | 2008108523 | 9/2008 |

OTHER PUBLICATIONS

International Search Report dated Jan. 3, 2008 issued in corresponding PCT Application No. PCT/KR2007/004631, 2 pages.

* cited by examiner

*Primary Examiner* — David H Willse
*Assistant Examiner* — Javier Blanco
(74) *Attorney, Agent, or Firm* — Edwards Wildman Palmer LLP; Kongsik Kim; Stephen D. LeBarron

(57) ABSTRACT

Disclosed is an intraocular lens supporter having a control ability. One embodiment of the present invention provides an intraocular lens supporter that is inserted into a capsular sac, including a first face coming in contact with an inner surface of the capsular sac in at least one point as a structural body that is extended along an equatorial region of the capsular sac; and a second face arranged opposite to the first face, wherein, in a section where the structural body is cut along a virtual plane in a visual axis direction (Y direction) of an eye lens, the first face is provided at a length as much as ¾ to 3 times of a length (d5, d10) of a region where an zonule of Zinn is coupled to an outer surface of the capsular sac.

10 Claims, 8 Drawing Sheets

INTRAOCULAR LENS SUPPORTER

CROSS-REFERENCE TO RELATED APPLICATION

This application is a U.S. National Filing of International PCT Application No. PCT/KR2007/004631 filed on Sep. 21, 2007, which claims priority to Korean Application No. 10-2007-0022870 filed Mar. 8, 2007, both of which are fully incorporated herein by reference.

TECHNICAL FIELD

The present invention relates to an intraocular lens supporter, and more particularly to an intraocular lens supporter capable of being provided inside a capsular sac to induce shape deformation of an intraocular lens.

BACKGROUND ART

In recent years, as one of treatment methods of ophthalmic diseases that are abnormal in eye lens such as cataract, a method has been increasingly used throughout the world, comprising steps of removing eye lens contents from a capsular sac and inserting an artificially produced intraocular lens into their space.

In the case of the insertion of the intraocular lens, the intraocular lens may give an opaque sight to patients instead of their own natural eye lens. However, regardless of its many advantages, the intraocular lens has problems that a capsular sac into which the intraocular lens is inserted is contracted after the insertion of the intraocular lens.

Accordingly, a new method has been increasingly used, comprising steps of inserting a capsular tension ring into an equatorial region of a capsular sac prior to the insertion of the intraocular lens and fixing the intraocular lens in the capsular tension ring.

A capsular tension ring, which is referred to as open or closed ring formations, is effective in partially relieving contraction of a capsular sac, partially maintaining a shape of the capsular sac from which an eye lens is removed, and easily supporting the inserted intraocular lens.

In order to use a capsular tension ring in a more effective manner, there have been recently ardent studies to develop a structure for easily inserting a capsular tension ring, a structure for preventing a posterior capsular opacity, etc.

However, a more serious problem in the conventional surgical operation of insertion of an intraocular lens is that an anterior capsule and a posterior capsule of a capsular sac are adhere to each other after the surgical operation, which leads to the loss of its inherent function to control a thickness of an eye lens by relaxing and contracting zonule of Zinn.

That is to say, the problems is that a patient does not ensure a sight through active three-dimensional movements of an intraocular lens along objects to be seen, but ensures a passive sight according to the predetermined power of an intraocular lens.

Hereinafter, the conventional surgical operation of insertion of an intraocular lens will be described in detail with reference to the accompanying drawings.

FIG. 1 is a cross-sectional view showing a human eyeball, and FIG. 2 is a cross-sectional view showing a structure of a natural eye lens. Referring to FIGS. 1 and 2, a cornea 10 is a transparent avascular tissue disposed in the outermost region of the eye and protects an eyeball. Also, the cornea serves to reflect the light together with the eye lens. An iris 20 functions as the iris of a camera by adjusting the intensity of the light entering the eye. Also, a pupil 30 is a hole in the center of the iris 20, and adjusts the intensity of the light entering the retina 40 by contracting the hole under the bright light and expanding the hole under the dark light.

An eye lens 50 is a colorless and transparent avascular structure having a convex lens shape in both sides, and arranged in the back of the iris 20. The eye lens 50 is an organ that takes part in reflecting the light entering the eye together with the cornea 10, and its shape is changed according to the contraction and relaxation of a ciliaris muscle 60 and a zonule of Zinn 70 coupled to the ciliaris muscle 60.

Presbyopia is a state that the hardness of the eye lens 50 increases with the age, and therefore the shape of the eye lens 50 is not changed even if the ciliaris muscle 60 contracts, and the cataract is a disease that the eye lens 50 becomes opaque with the age.

The eye lens 50 is filled inside a capsular sac 80, and the capsular sac 80 is composed of an anterior capsule 80*a* and a posterior capsule 80*b*, each of which is in contact with an anterior surface 51 and a posterior surface 55 of the eye lens 50. At this time, the anterior surface 51 and the posterior surface 55 of the eye lens 50 are coupled to each other in an equator (E). Each of the anterior surface 51 and the posterior surface 55 is divided into a central region (a) and an equatorial region (b) according to the distance from the equator (E). The central region (a) of the anterior surface 51 has a smaller curvature than the central region (a) of the posterior surface 55, and the equatorial region (b) of the anterior surface 51 has a larger curvature than the equatorial region (b) of the posterior surface 55.

The zonule of Zinn 70 is coupled along an edge of the capsular sac 80. The zonule of Zinn 70 is a kind of a fibrous tissue that couples the capsular sac 80 to the ciliaris muscle 60, and composed of a first zonule portion coupled to the center of the equatorial region in which the anterior capsule 80*a* and the posterior capsule 80*b* of the capsular sac 80 meets; and a second zonule portion coupled to a circumference of the equatorial region.

FIG. 3 and FIG. 4 are illustrative views showing an interaction of a zonule of Zinn, an eye lens and a capsular sac when focused on a long distance and a short distance object, respectively. In this application, a Y direction represents a visual axis direction of an eye lens, and an X direction represents an equatorial direction of an eye lens. The visual axis direction of the eye lens means a direction that the light enters an eye lens 50 through a pupil, and the equatorial direction means a direction that, as a vertical direction of the visual axis direction, connects a point that an anterior capsule and a posterior capsule of an eye lens meets.

In the zonule of Zinn 70, a first zonule portion 73 coupled to the center of the equatorial region of the capsular sac 80 is pulled taut and a second zonule portion 71 coupled to the circumference of the equatorial region of the capsular sac 80 is relaxed when focused on a long distance object. As a result, the capsular sac 80 is extended in an X direction of the eye lens 50, and therefore the eye lens 50 arranged inside the capsular sac 80 is extended in the same direction (X).

In the zonule of Zinn 70, the first zonule portion 73 coupled to the center of the equatorial region of the capsular sac 80 is relaxed and the second zonule portion 71 coupled to the circumference of the equatorial region of the capsular sac 80 is pulled taut when focused on a short distance object. As a result, the capsular sac 80 is projected in a Y direction of the eye lens 50, and therefore the eye lens 50 arranged inside the capsular sac 80 is extended in the same direction. As described above, the capsular sac 80 having a natural eye lens disposed therein is coupled to the zonule of Zinn 70, and therefore takes part in actively deforming shapes of the natural eye lens, but the use of the conventional intraocular lens and capsular tension ring forces the capsular sac to contract, which leads to the substantial loss of its functions.

In particular, a ciliaris muscle, which is coupled to a zonule of Zinn to take part in the shape deformation of an eye lens, is a visceral muscle that maintains the endless function to the death. Therefore, the conventional method of artificially removing an ability of healthy ciliaris muscle must be improved in that an ability of ciliaris muscle is not damaged although the eye lens is damaged.

Meanwhile, the conventional intraocular lens and capsular tension ring are disclosed in various literatures including U.S. Patent Publication Nos. 2006/0244904, 2006/0001186 and 2003/0149479.

DISCLOSURE OF INVENTION

Technical Problem

Accordingly, the present invention is designed to solve such drawbacks of the prior art, and therefore an object of the present invention is to provide an intraocular lens supporter that functions so that an intraocular lens moves in a similar manner to the movement of a natural eye lens by inducing shape deformation of the intraocular lens.

Technical Solution

One embodiment of the present invention is achieved by providing an intraocular lens supporter that is inserted into a capsular sac, including a first face coming in contact with an inner surface of the capsular sac in at least one point; and a second face arranged opposite to the first face, wherein, intraocular lens supporter is a structural body that is extended along an equatorial region of the capsular sac and in a section where the structural body is cut along a virtual plane in a visual axis direction (Y direction) of an eye lens, the first face is provided at a length as much as ¾ to 3 times of a length (d5, d10) of a region where a zonule of Zinn is coupled to an outer surface of the capsular sac.

At this time, the first face may have a length of 2 to 8 mm in the section where the structural body is cut along a virtual plane in a visual axis direction (Y direction) of an eye lens.

Also, the intraocular lens supporter may be a circular structural body whose both ends are coupled to each other.

Also, the intraocular lens supporter may be a circular structural body whose both ends are not coupled to each other.

Also, at least one section of the circular structural body may include a flexible connection unit that is made of a flexible material that is more flexible than the other section.

Also, the first face and the second face are preferably convex in a direction from the second face toward the first face.

Preferably, the first face has a first extended length from one end portion to the other end portion in the section where the first face is cut along a virtual plane in a visual axis direction (Y direction) of an eye lens, the second face has a second extended length from one end portion to the other end portion in the section where the second face is cut along a virtual plane in a visual axis direction (Y direction) of an eye lens, and the extended length of the second face is smaller than or identical to the extended length of the first face.

Also, the extended length of the second face is preferably longer as much as 0.4 to 1 times than the extended length of the first face.

Also, a space is preferably provided between the first face and the second face, and one selected from the group consisting of liquids, gases and solids is preferably included in the space.

Also, the first face may be composed of materials that are more flexible than the second face.

Also, materials of membranes constituting the first face and the second face are preferably identical to each other, and the membrane constituting the first face is preferably thinner than the membrane constituting the second face.

Also, the membrane constituting the first face and the membrane constituting the second face is preferably formed of the same materials in the same thickness.

Also, the liquid is preferably one selected from the group consisting of water, silicone, sodium hyaluronate, chondroitin sulfate, hydroxypropyl methylcellulose and polyacrylamide.

Also, the gas is preferably one selected from the group consisting of air, nitrogen, helium, neon and argon.

Also, the solid is preferably a fluent solid.

Also, the first face preferably has an anterior portion and a posterior portion corresponding respectively to an anterior capsule and a posterior capsule divided by means of an equator of the capsular sac, and the anterior portion preferably has a larger curvature than the posterior portion in the section where the first face is cut along a virtual plane in a visual axis direction (Y direction) of the eye lens.

Also, a sectional shape where the first face is cut along a virtual plane in a visual axis direction (Y direction) of the eye lens preferably accords with a sectional shape of an equatorial region of a human natural eye lens.

Also, an extended length from the equator to an end point of the anterior portion, and an extended length from the equator to an end point of the posterior portion preferably range from 1 to 4.2 mm in the sectional shape where the first face is cut along a virtual plane in a visual axis direction (Y direction) of the eye lens.

Also, the extended length from the equator to the end point of the anterior portion is preferably smaller than the extended length from the equator to the end point of the posterior portion.

Also, a material of the intraocular lens supporter is preferably composed of one selected from the group consisting of silicone, silicone elastomer, silicone polymer, polydimethyl siloxane, polypropylene, polyimide, polybutester, polymethyl methacrylate (PMMA), Microplex PMMA, CQ-UV PMMA, acrylic resin, rigid acrylic, flexible acrylic, acrylic plastic, hydrophobic acrylicHydrophobic acrylic, hydrophilic acrylic, hydrophilic acrylic polymer, UV absorbing acrylate, methacrylate copolymer, butyl acrylate, polysiloxane elastomer, UV absorbing polysiloxane, collagen copolymer, gold, hydrogel, 2-hydroxyethyl methacrylate (HEMA), methyl methacrylate (MMA), cellulose acetate butylate (CAB), 2-hydroxy ethyl methacrylate (2-HAMA), n-vinyl pyrrolidone (NVP), polyvinyl pyrrolidone (PVP), methacrylic acid (MA), glycerol methacrylate (GMA), dimethyl siloxane (DMS), polyhydroxyethyl methacrylate (PHEMA), polyethylenehlycol methacrylate (PEGMMA), poly HEMA hydrogel, poly HEMA hydrogel with UV absorption, silicone hydrogel, GMA/HEMA, HEMA/PVP/MA, PVA, HEMA/PVA/MA, HEMA/PVA/MMA, HEMA/MMA, HEMA/NVP, HEMA/NVP/MA, HEMA/NVP/MMA, HEMA/Acryl, and HEMA/PC.

Also, a surface of the first face is preferably rougher than a surface of the other face.

Also, the surface of the first face preferably further includes an adhesive for facilitating mounting of the capsular sac.

Also, the adhesive is preferably tissue glue or glue.

Also, the intraocular lens supporter is preferably a circular structural body whose first face has the same equatorial diameter as the inner surface of the capsular sac.

Advantageous Effects

The intraocular lens supporter according to the present invention has an effect to transfer a force to the intraocular lens to allow the intraocular lens to operate like the natural eye lens, the force being generated from the ciliaris muscle and transferred through the zonule of Zinn and the capsular sac.

Accordingly, the intraocular lens supporter according to the present invention may be used for the intraocular lens operation in order to treat cataract, presbyopia, high myopia, etc.

BRIEF DESCRIPTION OF THE DRAWINGS

These and/or other aspects and advantages of the invention will become apparent and more readily appreciated from the following description of the preferred embodiments, taken in conjunction with the accompanying drawings of which.

MODE FOR THE INVENTION

Hereinafter, preferable embodiments according to the present invention will be described with reference to the accompanying drawings.

Figure 1:
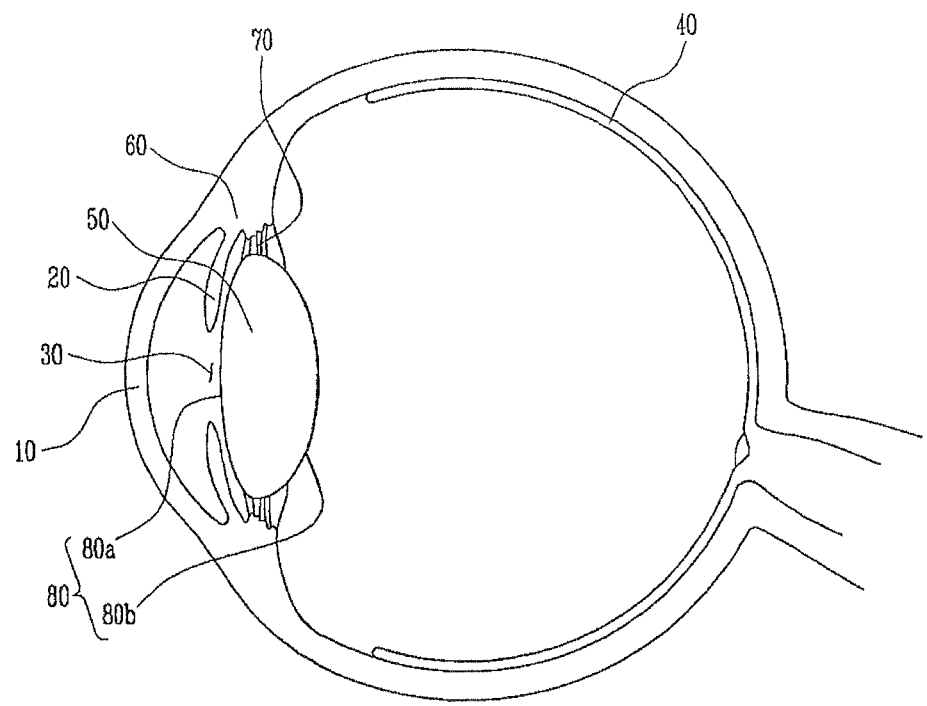
FIG. 1 is a cross-sectional view showing a human eyeball.
Figure 2:
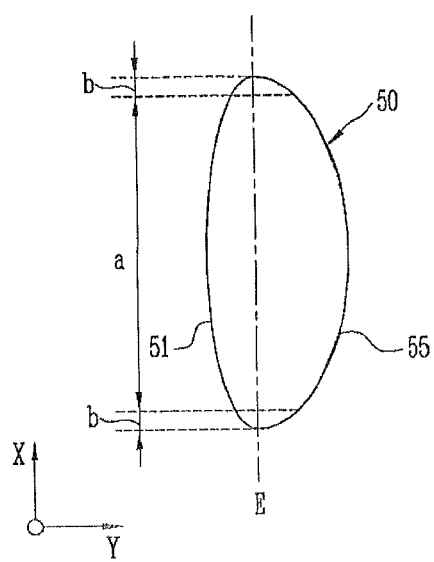
FIG. 2 is a cross-sectional view showing a structure of a natural eye lens.
Figure 3:
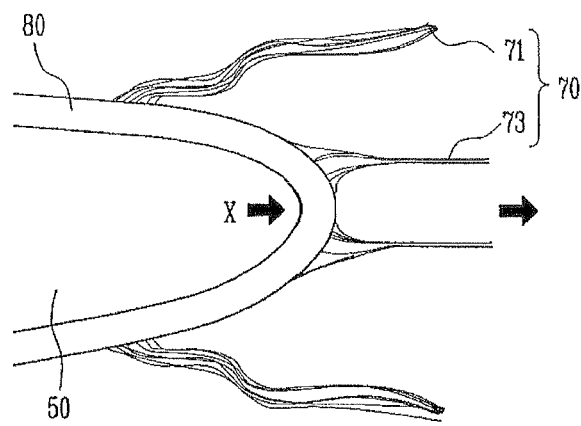
FIG. 3 and FIG. 4 are illustrative views showing interactions a zonule of Zinn, an eye lens and a capsular sac when focused on a long distance object first embodiment of the present invention.
Figure 4:
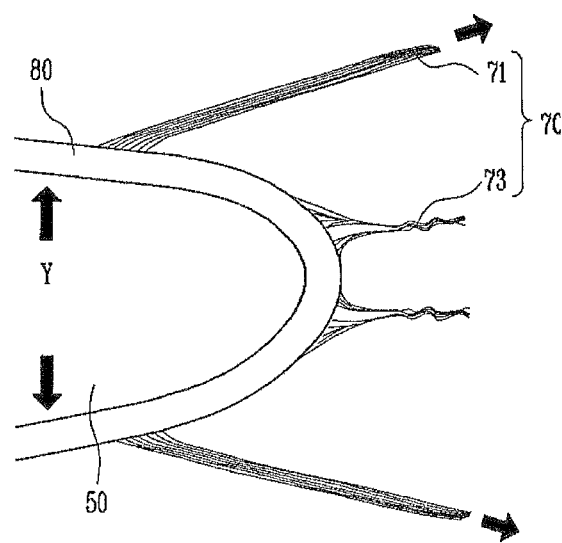
Figure 5:
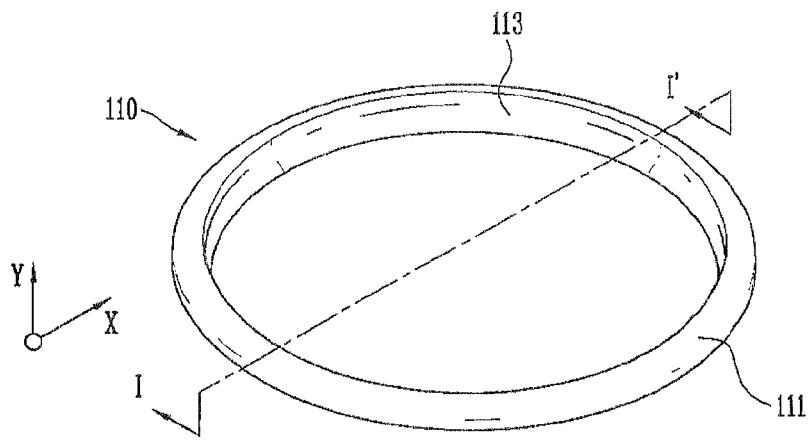
FIG. 5 is a perspective view showing an intraocular lens supporter according to the first embodiment of the present invention.

FIG. 5 is a cross-sectional view showing an intraocular lens supporter according to the first embodiment of the present invention. Referring to FIG. 5, the intraocular lens supporter 110 includes a first face 111 and a second face 113. The first face 111 and the second face 113 forms a structural body having a closed ring shape, and a space (not shown) is provide between a membrane constituting the first face 111 and a membrane constituting the second face 113. Materials and thickness of the membrane constituting the first face 111 and the second face 113 are not limited thereto, but a shape deformation ability by movement of the zonule of Zinn is further increased in the intraocular lens supporter 110 if flexible materials or thinner materials are used than if flexible materials or thinner materials are not used.

Meanwhile, the first face 111 and the second face 113 may be formed of the same materials and/or in the same thickness, or formed of the different materials and/or in a different thickness.

In order to improve a shape deformation ability according to the movement of the zonule of Zinn, the first face 111 may be composed of flexible materials that are more flexible than the second face 113. Also, if the first face 111 and the second face 113 are composed of the same materials, the first face 111 may be formed at a thinner thickness than the second face 113.

Meanwhile, the entire intraocular lens supporter 110 may be formed integrally in the first face 111 and the second face 113 without any of the empty space between the first face 111 and the second face 113 if the same solid materials as the materials constituting the first face 111 and the second face 113 are formed in the empty space.

The intraocular lens supporter 110 forms a ring-shaped structural body, and the first face 111 forms an outer surface of a ring and the second face 113 forms an inner surface of the ring, and therefore the entire extended length of the first face 111 is longer than the entire extended length of the second face 113 in an equatorial direction (X direction).

Also, a diameter of the intraocular lens supporter 110 is identical to a diameter of the inner surface of the capsular sac. The diameter may be varied according to the humans, but generally ranges from 9 to 13 mm, and a diameter of the equatorial region of the intraocular lens supporter 110 is preferably identical to a diameter of the inner surface of the equatorial region of the patient's eye lens.

A material of the intraocular lens supporter 110, as used herein, may include silicone, silicone elastomer, silicone polymer, polydimethyl siloxane, polypropylene, polyimide, polybutester, polymethyl methacrylate (PMMA), Microplex PMMA, CQ-UV PMMA, acrylic resin, rigid acrylic, flexible acrylic, acrylic plastic, hydrophobic acrylic (Hydrophobic acrylic), hydrophilic acrylic, hydrophilic acrylic polymer, UV absorbing acrylate, methacrylate copolymer, butyl acrylate, polysiloxane elastomer, UV absorbing polysiloxane, collagen copolymer, gold, hydrogel, 2-hydroxyethyl methacrylate (HEMA), methyl methacrylate (MMA), cellulose acetate butylate (CAB), 2-hydroxy ethyl methacrylate (2-HAMA), n-vinyl pyrrolidone (NVP), polyvinyl pyrrolidone (PVP), methacrylic acid (MA), glycerol methacrylate (GMA), dimethyl siloxane (DMS), polyhydroxyethyl methacrylate (PHEMA), polyethylenehlycol methacrylate (PEGMMA), poly HEMA hydrogel, poly HEMA hydrogel with UV absorption, silicone hydrogel, GMA/HEMA, HEMA/PVP/MA, PVA, HEMA/PVA/MA, HEMA/PVA/MMA, HEMA/MMA, HEMA/NVP, HEMA/NVP/MA, HEMA/NVP/MMA, HEMA/Acryl, and HEMA/PC.

Figure 6:
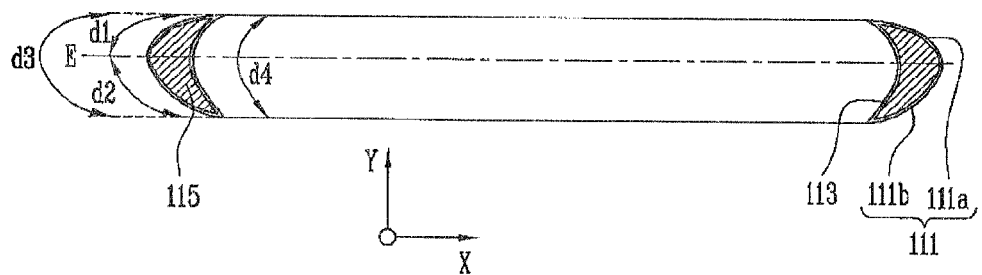
FIG. 6 is a cross-sectional view taken from a line I-I' as shown in FIG. 5.

FIG. 6 is a cross-sectional view taken from a line I-I' as shown in FIG. 5. Referring to FIG. 6, the first face 111 is a surface which is in contact with an inner surface of the capsular sac in at least one point, and the first face 111 is a section corresponding respectively to an anterior capsule and an posterior capsule of the capsular sac, and has an anterior portion 111a and a posterior portion 111b divided by an equator (E).

In a section cut along a virtual plane in a visual axis direction (Y direction) of the eye lens visual axis direction, the anterior portion 111a of the first face 111 has a larger curvature than the posterior portion 111b. This is why the section where the first face 111 is cut along a virtual plane in a visual axis direction (Y direction) of the eye lens is formed in the same shape as a sectional shape of an equatorial region of a natural eye lens. As described above, the anterior surface in the central region of the eye lens has a smaller curvature than the posterior surface, but the anterior surface and the posterior have a reverse shape as it approaches an equatorial region.

More particularly, the first face 111 is formed in the same sectional shape as the inherent eye lens of a patient that undergoes a surgical operation. A photograph of a sectional shape of the patient eye lens before the surgical operation is taken using ultrasonic imaging, CT, and MRI. The first face 111 has a sectional shape between mydriasis and miosis, but may have a shape that accord with the sectional shape of the eye lens having a pupil size of 3 to 4 mm.

Accordingly, the first face 111 accords with a shape of the inner surface in the equatorial region of the capsular sac.

In the section cut along a virtual plane in a visual axis direction (Y direction) of the eye lens, the first face 111 is preferably provided in a length as much as ¾ to 3 times of a length (d5, see FIG. 10) of a region where a zonule of Zinn is coupled to an outer surface of the capsular sac. A force transferred to the intraocular lens with the movement of the zonule of Zinn is not effectively transferred if the first face 111 is formed in a smaller length range than ¾ times, and the optic portion of the intraocular lens may be covered if the first face 111 is formed in a greater length range than 3 times. At this time, the first face 111 may have, for example, a length of 2 to 8 mm in the section where the structural body is cut along a virtual plane in a visual axis direction (Y direction) of the eye lens.

More preferably, an extended length (d1) from the equator (E) to an end point of the anterior portion 111a, and an extended length (d2) from the equator (E) to an end point of the posterior portion 111b may generally range from 1 to 4.2 mm in the section cut along a virtual plane in a visual axis direction (Y direction) of the eye lens. It is difficult to insert the intraocular lens supporter in the surgical operation and the optic portion is too small if the extended length exceeds 4.2 mm, whereas the intraocular lens supporter is provided in an inner position than a point where the second zonule portion of the zonule of Zinn as described later is coupled to the capsular sac if the extended length is less than 1 mm, and therefore a force transferred by the movement of the zonule of Zinn induced in the ciliaris muscle is not suitably transferred to the intraocular lens, which leads to insufficient volume change in the intraocular lens supporter.

At this time, the extended length (d1) from the equator (E) to the end point of the anterior portion 111a may be different from the extended length (d2) from the equator (E) to the end point of the posterior portion 111b, but the length of d2 will be generally longer than the length of d1.

Meanwhile, a roughness of the first face 111 may be higher or a separate adhesive may be added to facilitate mounting of the intraocular lens supporter 110 in the capsular sac. Therefore, the intraocular lens supporter 110 may be fixed in a stable position. A tissue glue or glue may be, for example, used as the adhesive.

The second face 113 is a surface to which the intraocular lens is coupled, and the total extended length (d4) in the section where the second face 113 is cut along a virtual plane in a visual axis direction (Y direction) of the eye lens is shorter than, or identical to the total extended length (d3=d1+d2) in the section where the first face 111 is cut along a virtual plane in a visual axis direction (Y direction) of the eye lens. A fact that the total extended length (d4) in the section where the second face 113 is cut along a virtual plane in a visual axis direction (Y direction) of the eye lens is smaller than or identical to the total extended length (d3=d1+d2) of the first face 111 is for the purpose of amplifying or maintaining a force transferred to the first face 111 when the force is transferred to the second face 113 in the zonule of Zinn.

That is to say, the movement and volume changes are more induced according to the movement of the first face 111 since the first face 111 has a shorter extended length than the second face 113. When a force F1 is transferred to the zonule of Zinn in the first face 111, a force transferred to the second face 113 becomes F2 (=kF1, k≥1). At this time, k is a constant determined by a length ratio of d3 and d4. The length ratio of d3 and d4 may be varied according to the ability of the zonule of Zinn in patients, and a length of d4 is preferably generally longer as much as 0.4 to 1 times than a length of d3.

An inner space between the first face 111 and the second face 113 is filled with gases, liquids or solids. The inner space may be filled with the gases, such as air or inert gases, namely, nitrogen, argon, neon, helium, etc., and filled with the liquids, such as water or silicone, sodium hyaluronate, chondroitin sulfate, hydroxypropyl methylcellulose, polyacrylamide, etc.

A shape deformation ability of the intraocular lens supporter 110 is more enhanced according to the movement of the zonule of Zinn of the intraocular lens supporter 110 if materials having a high fluidity are used as the materials filled in the space 115 between the first face 111 and the second face 113 than if materials having a high fluidity are not used.

Figure 7:
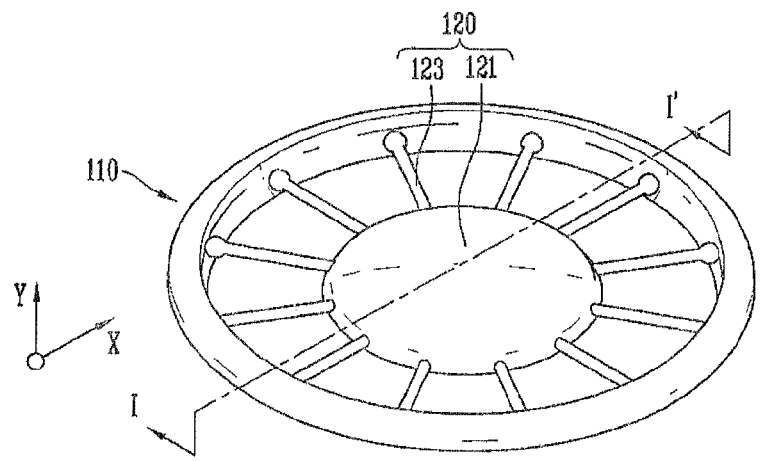
FIG. 7 is perspective view showing that an intraocular lens according to the first aspect is coupled to the intraocular lens supporter according to the first embodiment of the present invention.
Figure 8:
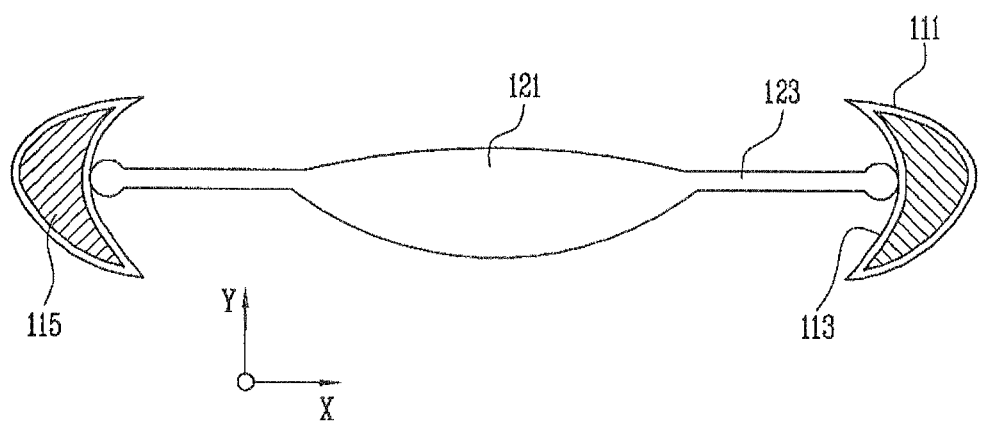
FIG. 8 is a cross-sectional view taken from a line I-I' as shown in FIG. 7.

FIG. 7 is perspective view showing that an intraocular lens is coupled to the intraocular lens supporter according to the first embodiment of the present invention, and FIG. 8 is a cross-sectional view taken from a line I-I' as shown in FIG. 7.

Referring to FIGS. 7 and 8, the intraocular lens 120 is supported by the intraocular lens supporter 110. The intraocular lens is formed inside a ring shape of the intraocular lens supporter 110. At this time, the haptic portion 123 of the intraocular lens 120 inserted inwardly into the capsular sac is in contact with the second face 111b of the intraocular lens supporter 110.

The intraocular lens 120 includes an optic portion 121 disposed in the rear of the pupil; and a haptic portion 123 coupled to the optic portion 121 to fix the optic portion 121 inside the capsular sac.

The intraocular lens 120 may be manufactured with various shapes, but the present invention is not particularly limited thereto. That is to say, the haptic portion 123 is coupled to an edge of the optic portion 121. At this time, the haptic portion 123 is composed at two or more numbers, and preferably 4 or more numbers.

Figure 9:
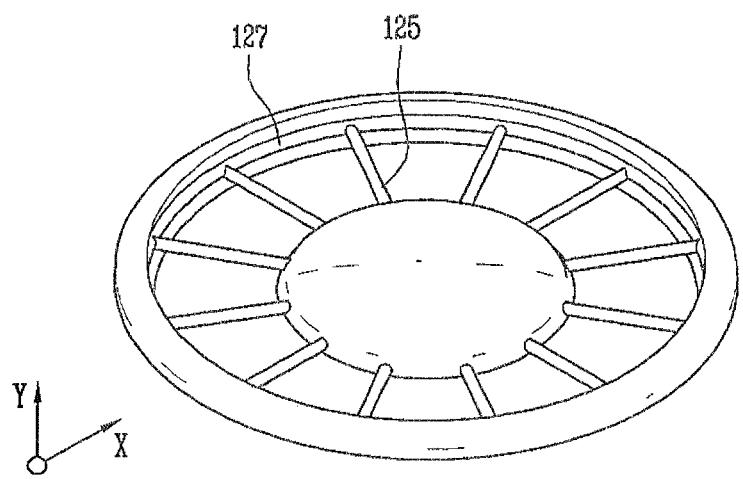
FIG. 9 is a perspective view showing that an intraocular lens according to the second aspect is coupled to the intraocular lens supporter according to the first embodiment of the present invention.

Meanwhile, the intraocular lens 120 may have a structure where the haptic portion 123 is composed of a plurality of shaft bars 125 and a ring-shaped support bar 127 coupled to an end of the shaft bar, as shown in FIG. 9. A force is more easily transferred to the optic portion according to the movement of the zonule of Zinn in the intraocular lens in which the support bar 127 is formed.

Hereinafter, an interaction of the intraocular lens according to the first embodiment of the present invention will be described in detail with reference to the accompanying drawings.

Figure 10:
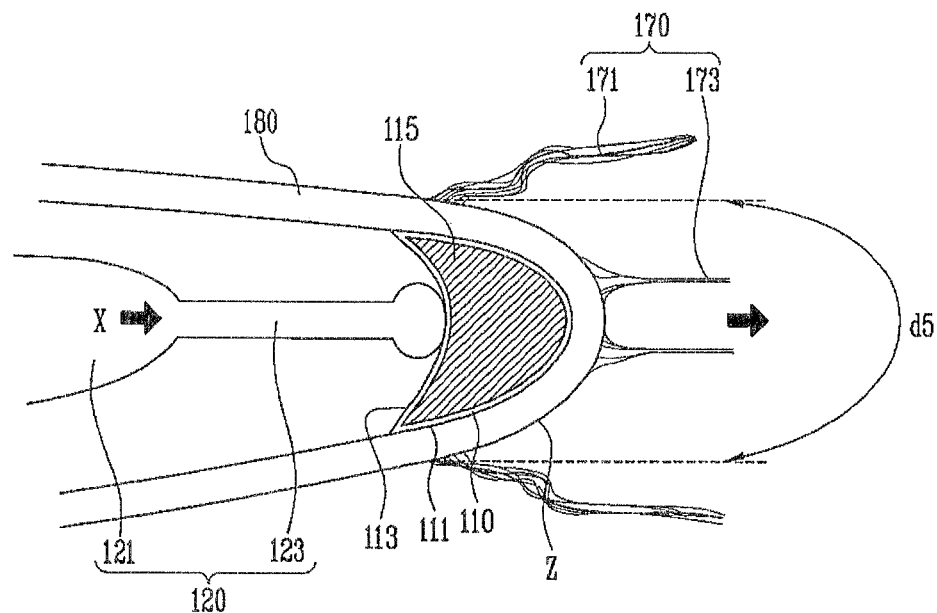
FIG. 10 and FIG. 11 are illustrative views showing interactions of a zonule of Zinn, an intraocular lens, an intraocular lens supporter and a capsular sac when focused on a long distance object and a short distance according to the first embodiment of the present invention.
Figure 11:
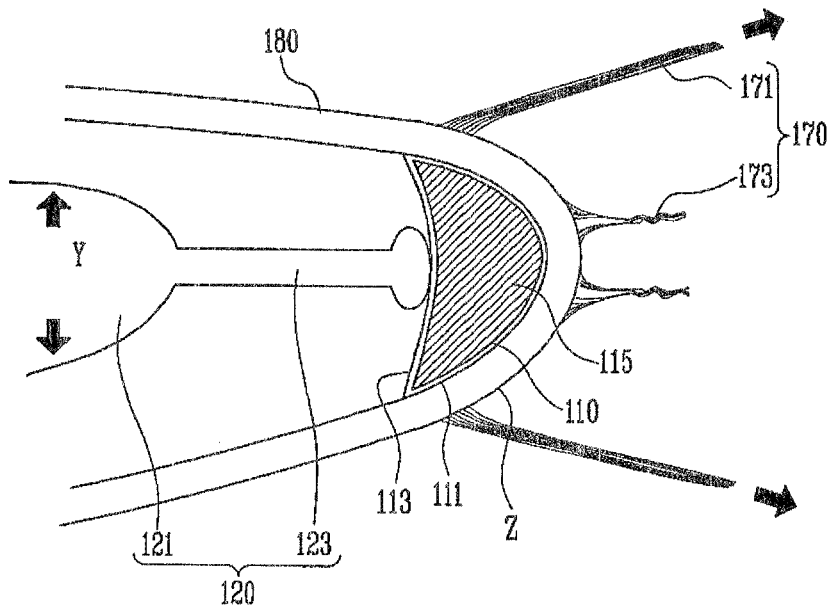

FIG. 10 and FIG. 11 are illustrative views showing interactions of a zonule of Zinn, an intraocular lens, an intraocular lens supporter and a capsular sac when focused on a long distance object and a short distance according to the first embodiment of the present invention.

The zonule of Zinn is coupled to the outer surface of the capsular sac, and the zonule of Zinn is coupled to a region around the equator of the capsular sac, and therefore a region to which the zonule of Zinn is coupled is referred to as a connection region for zonule of Zinn (Z) in this application.

When focused on a long distance object, a first zonule portion 173 coupled to the center of the connection region for zonule of Zinn (Z) in the capsular sac 180 is pulled taut, and a second zonule portion 171 coupled to a circumference of the equatorial region of the connection region for zonule of Zinn (Z) in the capsular sac 180 is relaxed. As a result, the equatorial region of the capsular sac 180 is subject to a force generated when extended in an X direction, and the intraocular lens 120 with elasticity arranged inside the capsular sac 180 is also extended in the same direction, which leads to the convex intraocular lens 120.

When focused on a short distance object, the first zonule portion 173 coupled to the center of the connection region for zonule of Zinn (Z) in the capsular sac 180 is relaxed, and the second zonule portion 171 coupled to a circumference of the connection region for zonule of Zinn (Z) in the capsular sac 180 is pulled taut. As a result, the equatorial region of the capsular sac 180 is protruded in a Y direction, and therefore the intraocular lens 120 with elasticity arranged inside the capsular sac 180 is extended in the same direction.

At this time, a shape deformation ability is further increased by a fluid 115 filled between the first face 111 and the second face 113, depending on the movement of the zonule of Zinn in the supporter.

Here, the Y direction is a visual axis direction of the eye lens, and the X direction is an equatorial direction of the eye lens.

As described above, the use of the intraocular lens supporter 110 according to this embodiment makes it the intraocular lens 120 possible to control its thickness like the natural eye lens. That is to say, as a thickness of the natural eye lens is controlled by the action of the capsular sac 180 coupled to the zonule of Zinn, the use of the intraocular lens supporter according to this embodiment makes it the intraocular lens possible to control its thickness.

Figure 12:
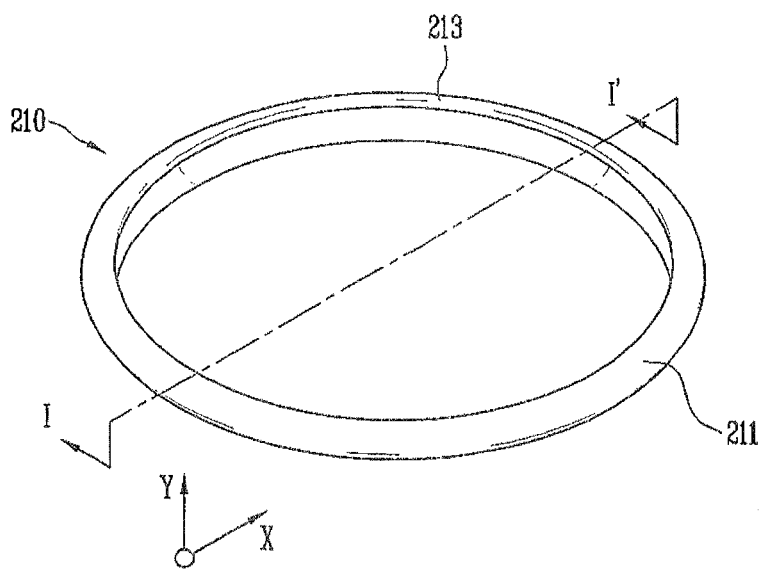
FIG. 12 is perspective view showing an intraocular and a short distance, respectively.

FIG. 12 is a perspective view showing an intraocular lens supporter according to the second embodiment of the present invention. The second embodiment is different from the first embodiment in that an empty space is formed between the first face 211 and the second face 213. Except for this difference, descriptions of the same parts will be described in brief. Referring to FIG. 12, the intraocular lens supporter 210 includes a first face 211 and a second face 213. Here, the first face 211 and the second face 213 constitute a closed integral ring-shaped structural body, and materials and thickness of the first face 211 and the second face 213 are not limited thereto, but a shape deformation ability by movement of the zonule of Zinn is generally further increased in the intraocular lens supporter 210 if flexible materials or thinner materials are used than if flexible materials or thinner materials are not used.

The intraocular lens supporter 210 forms a ring-shaped (spherical) structural body, and the first face 211 of the intraocular lens supporter 210 has the nearly same diameter as the inner surface of the capsular sac. Here, the diameter may be varied according to the humans, but generally ranges from 9 to 13 mm, and a diameter of the equatorial region of the intraocular lens supporter 210 is identical to a diameter of the inner surface of the equatorial region of the patient eye lens.

Used materials of the intraocular lens supporter 210 may be identical to the materials used in the first embodiment.

Figure 13:
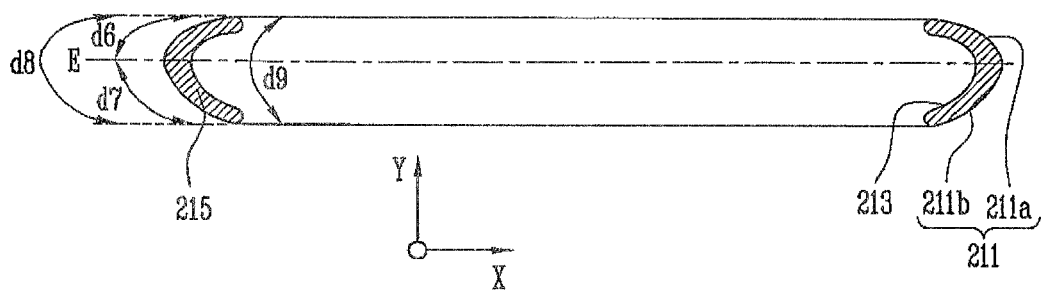
FIG. 13 is a cross-sectional view taken from a line I-I' as shown in FIG. 12.

FIG. 13 is a cross-sectional view taken from a line I-I' as shown in FIG. 12. Referring to FIG. 13, the first face 211 comes in contact with an inner surface of the capsular sac in at least one point, and the first face 211 has an anterior portion 211a and a posterior portion 211b that are divided by the equator (E) to correspond respectively to the anterior capsule and the posterior capsule of the capsular sac.

In the section cut along a virtual plane in a visual axis direction (Y direction) of the eye lens, the anterior portion 211a of the first face 211 has a larger curvature than the posterior portion 211b. This is for the purpose that the section cut along a radial direction (Y) of the first face 211 is formed in the same shape as the sectional shape of the equatorial region in the natural eye lens, and therefore this is why the anterior surface of the central region of the eye lens has a smaller curvature than the posterior surface, but has a reverse shape as it approaches the equatorial region, as described above.

More preferably, the first face 211 is formed in the same shape as the sectional shape of the inherent eye lens of a patient that undergoes a surgical operation. A photograph of a sectional shape of the patient eye lens before the surgical operation is taken using ultrasonic imaging, CT, and MRI. The first face 211 has a sectional shape between mydriasis and miosis, but may have a shape that accord with the sectional shape of the eye lens having a pupil size of 3 to 4 mm.

Accordingly, the first face 211 accords with a shape of the inner surface in the equatorial region of the capsular sac.

In the section cut along a virtual plane in a visual axis direction (Y direction) of the eye lens, the first face 211 is preferably provided in a length as much as ¾ to 3 times of a length (d10, see FIG. 14) of a region where a zonule of Zinn is coupled to an outer surface of the capsular sac. A force transferred to the intraocular lens with the movement of the zonule of Zinn is not effectively transferred if the first face 211 is formed in a smaller length range than ¾ times, and an optic portion of the intraocular lens may be covered if the first face 211 is formed in a smaller length range than 3 times. For example, the first face 211 may have a length of 2 to 8 mm in the section where the structural body is cut along a virtual plane in a visual axis direction (Y direction) of the eye lens.

More preferably, an extended length (d6) from the equator (E) to an end point of the anterior portion 211a, and an extended length (d7) from the equator (E) to an end point of the posterior portion 211b may generally range from 1 to 4.2 mm in the section cut along a virtual plane in a visual axis direction (Y direction) of the eye lens. It is difficult to insert the intraocular lens supporter in the surgical operation and the optic portion is too small if the extended length exceeds 4.2 mm, whereas the intraocular lens supporter is provided in an inner position than a point where the second zonule portion of the zonule of Zinn as described later is coupled to the capsular sac if the extended length is less than 1 mm, and therefore a force is not suitably transferred to the intraocular lens according to the movement of the zonule of Zinn induced in the ciliaris muscle, which leads to insufficient volume change in the intraocular lens supporter.

At this time, the extended length (d6) from the equator (E) to the end point of the anterior portion 211a may be different from the extended length (d7) from the equator (E) to the end point of the posterior portion 211b, but the length of d7 will be generally longer than the length of d6.

Meanwhile, a roughness of the first face 211 may be improved or a separate adhesive may be used to facilitate mounting of the intraocular lens supporter in the capsular sac. Therefore, the intraocular lens supporter may be fixed in a stable position. A tissue glue or glue may be, for example, used as the adhesive.

The second face 213 is a surface to which the intraocular lens is coupled, and the total extended length (d9) in the section where the second face 213 is cut along a virtual plane in a visual axis direction (Y direction) of the eye lens is shorter than, or identical to the total extended length (d8=d6+d7) in the section where the first face 211 is cut along a virtual plane in a visual axis direction (Y direction) of the eye lens. A fact that the total extended length (d9) in a radial direction (Y) of the second face 213 is smaller than or identical to the total extended length (d8=d6+d7) of the first face 211 is for the purpose of amplifying or maintaining a force transferred to the first face 211 when the force is transferred to the second face 213 in the zonule of Zinn.

That is to say, more movement and volume changes are induced according to the movement of the first face 211 since the second face 213 has a shorter extended length than the first face 211. When a force F1 is transferred to the zonule of Zinn in the first face 211, a force transferred to the second face 213 becomes F2 (=kF1, k≥1). At this time, k is a constant determined by a length ratio of d8 and d9. The length ratio of d8 and d9 may be varied according to the ability of the zonule of Zinn in patients, and a length of d9 is preferably longer as much as 0.4 to 1 times than a length of d8.

Figure 14:
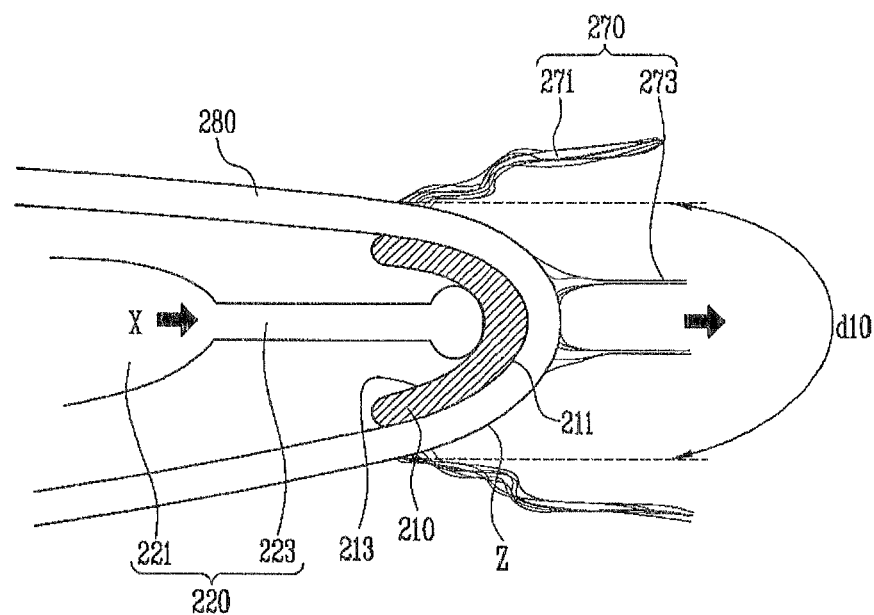
FIG. 14 and FIG. 15 are illustrative views showing interactions of a zonule of Zinn, an intraocular lens, an intraocular lens supporter and a capsular sac when focused on a long distance object and a short distance according to the second embodiment of the present invention.
Figure 15:
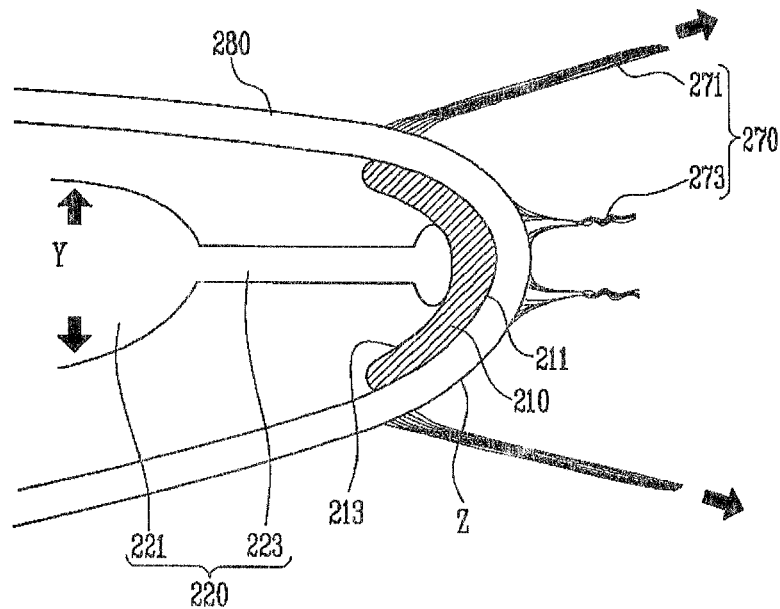

FIG. 14 and FIG. 15 are illustrative views showing interactions of a zonule of Zinn, an intraocular lens, an intraocular lens supporter and a capsular sac when focused on a long distance object and a short distance object according to the second embodiment of the present invention. The interactions according to this second embodiment are identical to the first embodiment, except that there is no fluid between the first face 211 and the second face 213. When focused on a long distance object, a first zonule portion 273 coupled to the center of the connection region for zonule of Zinn (Z) in the capsular sac 280 is pulled taut, and a second zonule portion 271 coupled to a circumference of the equatorial region of the connection region for zonule of Zinn (Z) in the capsular sac 280 is relaxed. As a result, the equatorial region of the capsular sac 180 is protruded in an X direction, and therefore the intraocular lens 220 with elasticity arranged inside the capsular sac 280 is extended in the same direction.

When focused on a short distance object, the first zonule portion 273 coupled to the center of the connection region for zonule of Zinn (Z) in the capsular sac 280 is relaxed, and the second zonule portion 271 coupled to a circumference of the connection region for zonule of Zinn (Z) in the capsular sac 280 is pulled taut. As a result, the equatorial region of the capsular sac 180 is protruded in a Y direction, and therefore the intraocular lens 220 with elasticity arranged inside the capsular sac 280 is extended in the same direction.

Here, the Y direction is a visual axis direction of the eye lens, and the X direction is an equatorial direction of the eye lens.

As described above, the use of the intraocular lens supporter 210 according to this embodiment makes it the intraocular lens 220 possible to control its thickness like the natural eye lens. That is to say, as a thickness of the natural eye lens is controlled by the action of the capsular sac 280 coupled to the zonule of Zinn, the use of the intraocular lens supporter according to this embodiment makes it the intraocular lens possible to control its thickness. In particular, the intraocular lens supporter 210 according to this embodiment has a poor transfer ability in the movement of the zonule of Zinn, compared to the first embodiment, and therefore the intraocular lens supporter 210 according to this embodiment will be suited for patients whose zonule of Zinn move more actively.

Figure 16:
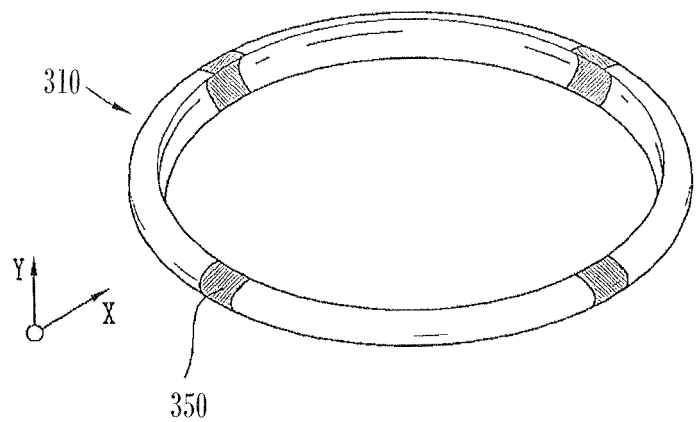
FIG. 16 is perspective view showing an intraocular lens supporter according to the third embodiment of the present invention.

FIG. 16 is perspective view showing an intraocular lens supporter according to the third embodiment of the present invention. Parts in the third embodiment that are overlapped with the first embodiment are not described herein, but different parts will be described herein. The intraocular lens supporter 310 according to the second embodiment is a closed ring-shaped structural body, and has a flexible connection unit 350 having at least one flexible region that is more flexible than other regions.

The flexible connection unit 350 is a cut region having a smaller area than the capsular sac, and aids to insert the intraocular lens supporter 310 into the capsular sac. That is to say, if the intraocular lens supporter 310 is inserted into the capsular sac, the flexible connection unit 350 is bended, and therefore the intraocular lens supporter 310 may be inserted into the capsular sac although it has a small cut region.

Figure 17:
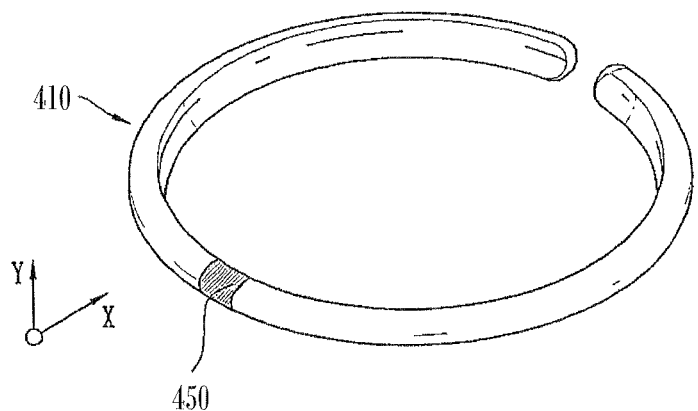
FIG. 17 is perspective view showing an intraocular lens supporter according to the fourth embodiment of the present invention.

FIG. 17 is perspective view showing an intraocular lens supporter according to the fourth embodiment of the present invention. The intraocular lens supporter 410 according to the fourth embodiment has an open ring-shaped structure other than the closed ring-shaped structure, and also has at least one flexible connection unit 450 like the third embodiment. As a result, the intraocular lens may be inserted into the capsular sac while the cut region is reduced to a smaller size in the surgical operations.

The description proposed herein is just a preferable example for the purpose of illustrations only, not intended to limit the scope of the invention, so it should be understood that other equivalents and modifications could be made thereto without departing from the spirit and scope of the invention as apparent to those skilled in the art. Therefore, it should be understood that the present invention might be not defined within the scope of which is described in detailed description but within the scope of which is defined in the claims and their equivalents.

What is claimed is:

1. An intraocular lens (IOL) supporter adapted to be inserted into a capsular sac, wherein the intraocular lens supporter is a structural body having a closed ring shape configured so that a force is transferred to the intraocular lens due to movement of a zonule of Zinn, the intraocular lens supporter comprising:

an outer circular face configured to come in direct contact with an inner surface of a capsular sac in at least one point when inserted into the capsular sac; and an inner circular face arranged opposite to the first face, the inner face comes in direct contact with a haptic portion of the intraocular lens, wherein the intraocular lens supporter is extended along an equatorial region of the capsular sac when inserted into the capsular sac and in a section where the structural body is cut along a virtual plane in a visual axis direction of an eye lens, the outer face is provided at a length as much as ¾ to 3 times of a length of a region where an zonule of Zinn is coupled to an outer surface of the capsular sac, the outer face has a first extended length from one end portion to another end portion in the section where the structural body of the outer face is cut along the virtual plane in the visual axis direction of the eye lens of 2 mm to 8 mm, the inner face has a second extended length from one end portion to another end portion on the section where the inner face is cut along the virtual plane in the visual axis direction of the eye lens, wherein the second extended length of the inner face is longer by 0.4 to 1 times that of the first extended length of the outer face, and the outer face has an anterior portion and a posterior portion corresponding respectively to an anterior capsule and a posterior capsule when inserted into the capsular sac divided by an equator (E) of the capsular sac, wherein the equator is a vertical direction relative to the visual axis direction of the eye lens.

2. The intraocular lens supporter according to claim 1, wherein the anterior portion has a larger curvature than the posterior portion, when viewed in an imaginary plane.

3. The intraocular lens supporter according to claim 1, wherein a sectional shape of the outer face taken by an imaginary plane accords with a sectional shape of an equatorial region of a human natural eye lens taken by the imaginary plane.

4. The intraocular lens supporter according to claim 1, wherein a material of the intraocular lens supporter is composed of one selected from the group consisting of silicone, silicone elastomer, silicone polymer, polydimethyl siloxane, polypropylene, polyimide, polybutester, polymethyl methacrylate (PMMA), Microplex PMMA, CQ-UV PMMA, acrylic resin, rigid acrylic, flexible acrylic, acrylic plastic, hydrophobic acrylicHydrophobic acrylic, hydrophilic acrylic, hydrophilic acrylic polymer, UV absorbing acrylate, methacrylate copolymer, butyl acrylate, polysiloxane elastomer, UV absorbing polysiloxane, collagen copolymer, gold, hydrogel, 2-hydroxyethyl methacrylate (HEMA), methyl methacrylate (MMA), cellulose acetate butylate (CAB), 2-hydroxy ethyl methacrylate (2-HAMA), n-vinyl pyrrolidone (NVP), polyvinyl pyrrolidone (PVP), meth acrylic acid (MA), glycerol methacrylate (GM A), dimethyl siloxane (DMS), polyhydroxyethyl methacrylate (PHEMA), polyethylenehlycol methacrylate (PEGMMA), poly HEMA hydrogel, poly HEMA hydrogel with UV absorption, silicone hydrogel, GMA/HEMA, HEMA/PVP/MA, PVA, HEMA/PVA/MA, HEMA/PVA/MMA, HEMA/MMA, HEMA/NVP, HEMA/NVP/MA, HEMA/NVP/MM A, HEM A/Acryl, and HEM A/PC.

5. The intraocular lens supporter according to claim 1, wherein a surface of the outer face is rougher than a surface of the inner face.

6. The intraocular lens supporter according to claim 1, wherein a surface of the outer face further includes an adhesive for facilitating mounting of the capsular sac.

7. The intraocular lens supporter according to claim 6, wherein the adhesive is tissue glue or glue.

8. The intraocular lens supporter according to claim 1, wherein the outer face has the same or substantially same equatorial diameter as the inner surface of the capsular sac.

9. The intraocular lens supporter according to claim 1, wherein the outer face and the inner face are convex in a direction from the inner face toward the outer face.

10. The intraocular lens supporter according to claim 1, wherein a fluid is filled between the first face and the second face.

* * * * *